US009013091B2

(12) United States Patent
Wada

(10) Patent No.: US 9,013,091 B2
(45) Date of Patent: Apr. 21, 2015

(54) PHOTOACOUSTIC IMAGING APPARATUS, PHOTOACOUSTIC IMAGING METHOD, AND PROBE FOR PHOTOACOUSTIC IMAGING APPARATUS

(71) Applicant: FUJIFILM Corporation, Minato-ku, Tokyo (JP)

(72) Inventor: Takatsugu Wada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 81 days.

(21) Appl. No.: 14/025,953

(22) Filed: Sep. 13, 2013

(65) Prior Publication Data
US 2014/0018660 A1    Jan. 16, 2014

Related U.S. Application Data

(63) Continuation of application No. PCT/JP2012/001710, filed on Mar. 13, 2012.

(30) Foreign Application Priority Data

Mar. 16, 2011  (JP) ................................ 2011-057738

(51) Int. Cl.
*B06B 1/06* (2006.01)
*A61B 5/00* (2006.01)
(Continued)

(52) U.S. Cl.
CPC .............. *A61B 5/0095* (2013.01); *B06B 1/0607* (2013.01); *A61B 8/4411* (2013.01); *A61B 8/4427* (2013.01); *A61B 8/4455* (2013.01); *A61B 8/4483* (2013.01); *A61B 8/5261* (2013.01)

(58) Field of Classification Search
CPC .. A61B 5/0095; A61B 8/4411; A61B 8/4427; A61B 8/4455; A61B 8/4483; A61B 8/5261; B06B 1/06; B06B 1/0607; B06B 1/0611; B06B 1/064; B06B 1/0688
USPC ................................................... 310/334, 335
See application file for complete search history.

(56) References Cited

U.S. PATENT DOCUMENTS 6,308,389 B1  10/2001  Tezuka
6,625,856 B2   9/2003  Tezuka
(Continued)

FOREIGN PATENT DOCUMENTS

CN      1575770 A     2/2005
JP    06-148154 A     5/1994
(Continued)

OTHER PUBLICATIONS

Communication dated Sep. 11, 2014 from the State Intellectual Property Office of the People's Republic of China in counterpart Chinese Patent Application No. 201280013515.4.
(Continued)

*Primary Examiner* — Derek Rosenau
(74) *Attorney, Agent, or Firm* — Sughrue Mion, PLLC

(57) ABSTRACT

Acoustic waves and photoacoustic waves are detected efficiently in a photoacoustic imaging apparatus configured to obtain acoustic images as well, to enable obtainment of high quality acoustic images and photoacoustic images. A probe for a photoacoustic imaging apparatus is equipped with: first piezoelectric bodies that detect acoustic waves reflected by a subject after the acoustic waves are irradiated onto the subject; and second piezoelectric bodies that detect photoacoustic waves generated within the subject due to irradiation of light after the light is irradiated onto the subject. Piezoelectric bodies made from an inorganic material are employed as the first piezoelectric bodies, and piezoelectric bodies made from an organic material are employed as the second piezoelectric bodies.

20 Claims, 2 Drawing Sheets

(51) Int. Cl.
*A61B 8/00* (2006.01)
*A61B 8/08* (2006.01)

(56) References Cited

U.S. PATENT DOCUMENTS

| | | | |
|---|---|---|---|
| 6,979,292 B2 | 12/2005 | Kanayama et al. | |
| 8,531,178 B2 * | 9/2013 | Sasaki | 310/334 |
| 2009/0005685 A1 * | 1/2009 | Nagae et al. | 600/459 |
| 2011/0088477 A1 | 4/2011 | Someda et al. | |
| 2012/0123256 A1 | 5/2012 | Razansky et al. | |

FOREIGN PATENT DOCUMENTS

| | | |
|---|---|---|
| JP | 2000-166923 A | 6/2000 |
| JP | 2004-104629 A | 4/2004 |
| JP | 2004-351023 A | 12/2004 |
| JP | 2008-049063 A | 3/2008 |
| JP | 2010-022816 A | 2/2010 |
| JP | 2010-125260 A | 6/2010 |
| JP | 2010-165771 A | 7/2010 |
| JP | 2010-182994 A | 8/2010 |
| JP | 2011-018682 A | 1/2011 |
| JP | 2011-045514 A | 3/2011 |
| WO | 2011-000389 A1 | 1/2011 |

OTHER PUBLICATIONS

Office Action, dated Apr. 8, 2014, issued by the Japanese Patent Office in counterpart Japanese Patent Application No. 2011-057738.

* cited by examiner

PHOTOACOUSTIC IMAGING APPARATUS, PHOTOACOUSTIC IMAGING METHOD, AND PROBE FOR PHOTOACOUSTIC IMAGING APPARATUS

TECHNICAL FIELD

The present invention is related to a photoacoustic imaging apparatus, that is, an apparatus that irradiates light onto a subject such as living tissue, and images the subject based on acoustic waves which are generated accompanying the irradiation of light. More specifically, the present invention is related to a photoacoustic imaging apparatus that also has a function of obtaining ultrasound images. In addition, the present invention is also related to a photoacoustic imaging method.

Further, the present invention is related to a probe to be employed by the photoacoustic imaging apparatus.

BACKGROUND ART

Conventionally, photoacoustic imaging apparatuses that image the interiors of living organisms utilizing the photoacoustic effect are known, as disclosed in U.S. Pat. No. 6,979, 292 and X. Wang et al., "A High-Speed Photoacoustic Tomography System based on a Commercial Ultrasound and a Custom Transducer Array", Proc. of SPIE, Vol. 7564, pp. 756424-1-756424-9, 2010. Photoacoustic imaging apparatuses irradiate pulsed light such as pulsed laser beam into the living organisms. Biological tissue that absorbs the energy of the pulsed light generates acoustic waves (acoustic signals) by volume expansion thereof due to heat. The acoustic waves are detected by an ultrasound probe or the like, and the detected signals are utilized to enable visualization of the living organisms based on acoustic waves.

Meanwhile, ultrasound imaging apparatuses that employ ultrasound probes are also conventionally known, as disclosed in Japanese Unexamined Patent Publication No. 6(1994)-148154. Such ultrasound probes are equipped with ultrasonic transducers (hereinafter, abbreviated as "UT") at the leading ends thereof. In many cases, the probes are constituted by a backing material, piezoelectric bodies, electrodes having the piezoelectric bodies sandwiched therebetween, acoustic matching layers, acoustic lenses, etc. In ultrasound imaging apparatuses, ultrasonic waves are irradiated from the UT's to subjects (human bodies), and reflected acoustic waves from the subjects are received by the UT's.

Ultrasound images are obtained by electrically processing detected signals of the reflected acoustic waves.

Note that it is also possible to obtain ultrasound tomographic images by scanning and irradiating ultrasonic waves. Known methods for obtaining ultrasound tomographic images include: the mechanical scanning method, in which UT's are mechanically rotated, swung, or slid; and the electronic scanning method, in which a plurality of UT's are provided as an array (hereinafter, referred to as "UT array") and UT's to be driven are selectively switched by electronic switches or the like.

Such ultrasound probes are capable of detecting acoustic waves as well as ultrasonic waves. Therefore, an apparatus capable of obtaining both photoacoustic images and ultrasound images is being proposed. That is, a light irradiating section that irradiates light onto subjects is added to an ultrasound probe of this type of apparatus, and acoustic waves generated by the subjects due to irradiation of light are detected by the UT's of the ultrasound probe.

DISCLOSURE OF THE INVENTION

An object of the present invention is to enable obtainment of high quality ultrasound images and photoacoustic images, by efficiently detecting ultrasonic waves and acoustic waves in a photoacoustic imaging apparatus configured to obtain ultrasound images as well.

Another object of the present invention is to provide a probe for a photoacoustic imaging apparatus capable of efficiently detecting ultrasonic waves and acoustic waves.

A probe for a photoacoustic imaging apparatus of the present invention comprises:

a light irradiating section that outputs light to be irradiated onto a subject such that photoacoustic waves are generated;

an acoustic wave generating section that generates and outputs acoustic waves to be irradiated onto the subject:

first piezoelectric bodies that detect the acoustic waves which are reflected by the subject; and second piezoelectric bodies that detect photoacoustic waves generated within the subject due to irradiation of the light;

piezoelectric bodies made from an inorganic material being employed as the first piezoelectric bodies; and piezoelectric bodies made from an organic material being employed as the second piezoelectric bodies.

It is desirable for an acoustic matching layer that also functions as an electrode common to the first and second piezoelectric bodies, to be formed between the first and second piezoelectric bodies.

It is also desirable for the second piezoelectric bodies to be provided more toward the subject than the first piezoelectric bodies.

Here, it is desirable for the acoustic matching layer to contain metal. In addition, it is desirable for the acoustic matching layer to be a composite of an organic material and a metal. It is also desirable for such an organic material of the acoustic matching layer to have adhesive properties.

Further, it is preferable for the metal to be metal nanoparticles.

Alternatively, the acoustic matching layer may be one of a material having relatively low conductive properties or a material having no conductive properties, the surface of the material being covered with a material having conductive properties.

Meanwhile, a photoacoustic imaging method of the present invention is that which is equipped with a probe for a photoacoustic imaging apparatus of the present invention.

In addition, a photoacoustic imaging method of the present invention is that which employs a probe for a photoacoustic imaging apparatus of the present invention to obtain acoustic images based on signals output by the first piezoelectric bodies, and to obtain photoacoustic images based on signals output by the second piezoelectric bodies.

Commonly, the frequencies of ultrasonic waves which are irradiated onto subjects such as living tissue to obtain ultrasound images are within a limited range within a range from 1 MHz to 40 MHz (approximately 80% of a fractional bandwidth at 6 dB, such as a range from 2 MHz to 5 MHz, a range from 4 MHz to 10 MHz, or a range of 5 MHz to 12 MHz, for example). In contrast, although the frequencies of acoustic waves which are generated by subjects such as living tissue due to irradiation of light are also within a range from 1 MHz to 40 MHz, the frequencies of the acoustic waves are spread out evenly across the entire frequency range from 1 MHz to 40 MHz. Meanwhile, piezoelectric bodies formed by inorganic materials have extremely high detection sensitivity within comparatively narrow bandwidths (approximately 80% of a fractional bandwidth at 6 dB), while piezoelectric bodies formed by organic materials do not exhibit a clear resonance point in the structure of a probe, and therefore have comparatively high detection sensitivity across an extremely wide frequency bandwidth.

The probe for a photoacoustic imaging apparatus of the present invention detects comparatively low frequency ultrasound waves, which have low level tissue attenuation, with the first piezoelectric bodies made from an inorganic material having the above properties. In addition, the second piezoelectric bodies made from an organic material having the above properties detect acoustic waves. Therefore, the probe of the present invention is capable of efficiently detecting reflected ultrasonic waves, while detecting acoustic waves across a wide frequency range.

The photoacoustic imaging apparatus of the present invention that employs the probe of the present invention efficiently detects reflected ultrasonic waves and acoustic waves. Accordingly, the photoacoustic imaging apparatus of the present invention is capable of obtaining ultrasound images and photoacoustic images having high image quality.

BEST MODE FOR CARRYING OUT THE INVENTION

Figure 1:
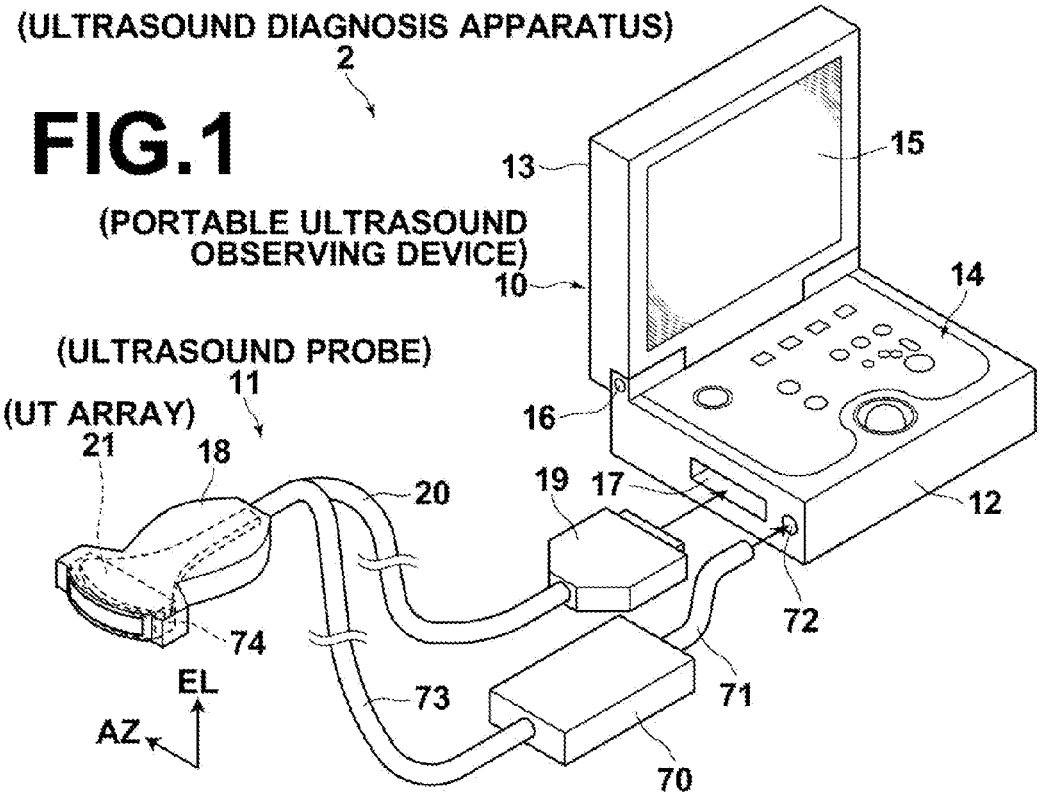
FIG. 1 is a perspective view that illustrates the entirety of a photoacoustic imaging apparatus according to an embodiment of the present invention.
Figure 2:
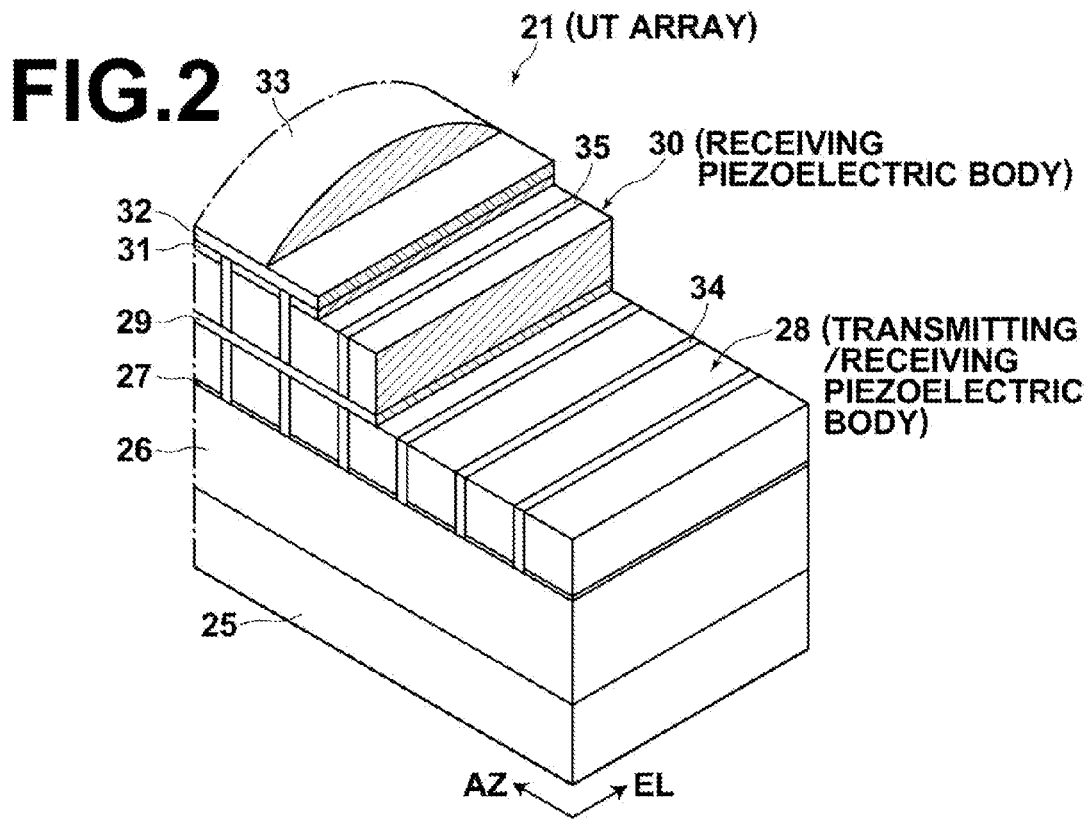
FIG. 2 is a partially sectional perspective view that illustrates a probe for a photoacoustic apparatus according to the embodiment of the present invention.
Figure 3:
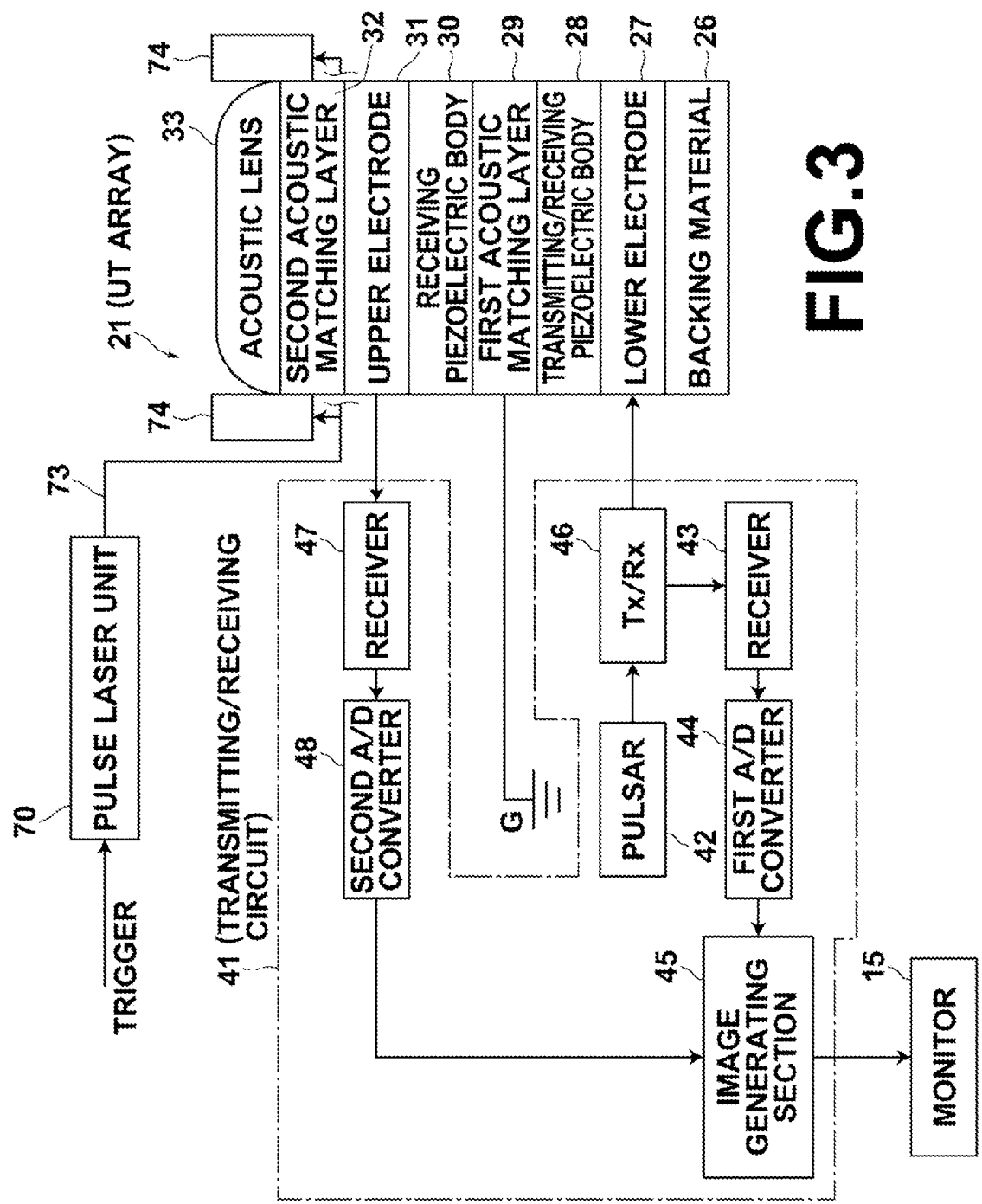
FIG. 3 is a block diagram that illustrates the electrical configuration of the photoacoustic imaging apparatus.

Hereinafter, an embodiment of the present invention will be described in detail with reference to the attached drawings. FIG. 1 is a perspective view that illustrates the entirety of a photoacoustic imaging apparatus according to an embodiment of the present invention. FIG. 2 is a partially sectional perspective view that illustrates a probe employed by the photoacoustic imaging apparatus. FIG. 3 is a block diagram that illustrates the electrical configuration of the photoacoustic imaging apparatus of the present embodiment.

The apparatus of the present embodiment is configured as an ultrasound diagnosis apparatus 2. The ultrasound diagnosis apparatus 2 is basically constituted by: a portable ultrasonic wave observing device 10; an external ultrasound probe (probe for a photoacoustic imaging apparatus) 11; and a pulse laser unit 70, as illustrated in FIG. 1.

The portable ultrasonic wave observing device 10 includes an apparatus main body 12 and a cover 13. An operating section 14 having a plurality of buttons and a trackball for inputting various operational commands into the portable ultrasonic wave observing device 10 is provided on the upper surface of the apparatus main body 12. A monitor 15 that displays various operating screens in addition to ultrasound images is provided on the inner surface of the cover 13.

The cover 13 is mounted to the apparatus main body 12 via a hinge 16, and is rotatable between an open position, in which the operating section 14 and the monitor 15 are exposed as illustrated in FIG. 1, and a closed position (not shown) in which the operating section 14 and the monitor 15 are both covered and protected. A grip (not shown) is mounted on a side surface of the apparatus main body 12, to enable the portable ultrasonic wave observing device 10 to be carried in a state in which the apparatus main body 12 and the cover 13 are closed. A probe connecting section 17 and a laser unit connecting section 72 are provided on the other side surface of the apparatus main body 12.

The ultrasound probe 11 includes: a scanning head 18 which is held by an operator and pressed against subjects; a connector 19 to be connected to the probe connecting section 17; and a cable 20 that connects the scanning head 18 and the connector 19. An ultrasonic wave transducer array (hereinafter, abbreviated as "UT array") 21 is built in to the leading end portion of the scanning head 18.

As illustrated in FIG. 2, the UT array 21 has a structure in which a backing material 26, a lower electrode 27, ultrasonic wave transmitting/receiving piezoelectric bodies 28, a first acoustic matching layer 29, acoustic wave receiving piezoelectric bodies 30, an upper electrode 31, a second acoustic matching layer 32, and an acoustic lens 33 are stacked in this order on a planar base 25 formed by glass-epoxy resin or the like.

The backing material 26 restricts free vibration of the ultrasonic wave transmitting/receiving piezoelectric bodies 28 when they radiate ultrasonic waves, and improves resolution in the direction that the ultrasonic waves propagate. Various materials capable of absorbing vibration may be employed as the backing material 26. The backing material may be an inorganic material or an organic material. Resin materials such as epoxy series resins and rubber materials such as chlorinated polyethylene rubber, natural rubber, and SBR are preferable, because these materials have low acoustic impedances and can absorb vibrations without decreasing sensitivity.

The ultrasonic wave transmitting/receiving piezoelectric bodies 28 are the first piezoelectric bodies of the present invention. The ultrasonic wave transmitting/receiving piezoelectric bodies 28 are shaped as long strips that extend in the EL direction. A plurality of the ultrasonic wave transmitting/receiving piezoelectric bodies 28 are provided at equidistant intervals in the azimuth direction (hereinafter, abbreviated as "AZ direction") perpendicular to the EL direction. The gaps among the ultrasonic wave transmitting/receiving piezoelectric bodies 28 and the peripheries thereof are filled with a filling agent 34.

The thickness of the ultrasonic wave transmitting/receiving piezoelectric bodies 28 is within a range from 0.1 mm to 0.5 mm. The ultrasonic wave transmitting/receiving piezoelectric bodies 28 are sandwiched from above and below by the first acoustic matching layer 29 and the lower electrode 27. The first acoustic matching layer 29 has conductive properties, and also functions as the upper electrode of the ultrasonic wave transmitting/receiving piezoelectric bodies 28. The lower electrode 27 is formed by a thin metal film, for example. Lead wires (not shown) are connected to each of the first acoustic matching layer 29 and the lower electrode 27. The combination of the lower electrode 27, the ultrasonic wave transmitting/receiving piezoelectric bodies 28, and the first acoustic matching layer 29 constitute a transmitting/receiving ultrasonic wave transducer.

The lead wire connected to the first acoustic matching layer 29 is grounded (refer to FIG. 3). Meanwhile, the lead wire connected to the lower electrode 27 is connected to the portable ultrasonic wave observing device 10. A transmitting/receiving circuit 41 (refer to FIG. 3) is built in the portable ultrasonic wave observing device 10. When pulsed voltages are applied from the transmitting/receiving circuit 41 to the ultrasonic wave transmitting/receiving piezoelectric bodies 28, the ultrasonic wave transmitting/receiving piezoelectric bodies 28 vibrate and generate ultrasonic waves. Thereby, ultrasonic waves are irradiated onto observation target portions of subjects. In addition, when reflected waves are received from observation target portions, the ultrasonic wave transmitting/receiving piezoelectric bodies 28 vibrate and generate voltages. The generated voltages are output as received signals.

Various inorganic materials that exhibit piezoelectric properties are employed as the material of the ultrasonic wave transmitting/receiving piezoelectric bodies 28. Pb series piezoelectric materials having PZT as a main component are extremely preferable. Particularly, relaxer system piezoelectric single crystals such as PMN-PT and PZN-PT, the use of which is becoming prevalent recently as materials that exhibit extremely high piezoelectric constants, are preferable. These materials have high electromechanical bonding coefficients k, and the ratio of ultrasonic wave output with respect to applied voltages (conversion efficiency) is comparatively high.

The acoustic wave receiving piezoelectric bodies 30 are the second piezoelectric bodies of the present invention, and are provided as dedicated receivers of acoustic waves which will be described later. The acoustic wave receiving piezoelectric bodies 30 also function as an acoustic matching layer that moderates the difference in acoustic impedances of the ultrasonic wave transmitting/receiving piezoelectric bodies 28 and the human body in a stepwise manner, to improve the transmitting and receiving sensitivity with respect to ultrasonic waves. In addition, the second acoustic matching layer 32 moderates the difference in acoustic impedances of the human body and the acoustic wave receiving piezoelectric bodies 30 in a stepwise manner, to improve the reception sensitivity with respect to ultrasonic waves.

Various conductive materials having an acoustic impedance less than that of the ultrasonic wave transmitting/receiving piezoelectric bodies 28 and greater than that of the acoustic wave receiving piezoelectric bodies 30 may be employed as the material of the first acoustic matching layer 29. A specific example of the first acoustic matching layer 29 is a sintered mixture of a resin having adhesive properties and metal nanoparticles (metal particles having diameters within a range from 1 nm to 100 nm). The metal nanoparticles may include silver nanoparticles, and preferably all of the metal nanoparticles are silver nanoparticles. Silver nanoparticles have comparatively high dispersion properties among metal nanoparticles with respect to resin, and are therefore preferable. When a resin that contains metal nanoparticles is sintered, the particles bond with each other within the resin to form conductive paths. Thereby, a high degree of conductivity can be obtained. Note that the first acoustic matching layer 29 may be a material having relatively low conductive properties or a material having no conductive properties, as long as the surface of the material is covered by a material having conductive properties.

A plurality of the acoustic wave receiving piezoelectric bodies 30 may be arranged in a manner similar to that of the ultrasonic wave transmitting/receiving piezoelectric bodies 28. Alternatively, the acoustic wave receiving piezoelectric bodies 30 may be in the form of a sheet which is electrically divided by electrodes patterned as strips. The gaps among the acoustic wave receiving piezoelectric bodies 30 and the peripheries thereof are filled with the filling agent 35.

The thickness of the acoustic wave receiving piezoelectric bodies 30 is within a range from 0.05 mm to 0.3 mm. The acoustic wave receiving piezoelectric bodies 30 are sandwiched from above and below by the upper electrode 31 and the first acoustic matching layer 29. As described above, the first acoustic matching layer has conductive properties, and also functions as the upper electrode of the ultrasonic wave transmitting/receiving piezoelectric bodies 28. The first acoustic matching layer further functions as a lower electrode of the acoustic wave receiving piezoelectric bodies 30. that is, the first acoustic matching layer 29 functions as an electrode common to the ultrasonic wave transmitting/receiving piezoelectric bodies 28 and the acoustic wave receiving piezoelectric bodies 30. The upper electrode 31 is constituted by a thin metal film, for example, and has a lead wire (not shown) connected thereto.

The lead wire connected to the upper electrode 31 is connected to the portable ultrasonic wave observing device 10. When the acoustic wave receiving piezoelectric bodies 30 receive reflected waves, received signals are input to a transmitting/receiving circuit 41 (refer to FIG. 3) built in to the portable ultrasonic wave observing device 10. The combination of the first acoustic matching layer 29, the acoustic wave receiving piezoelectric bodies 30, and the upper electrode 31 constitute receiving ultrasonic wave transducers.

Various organic materials having an acoustic impedance less than that of the first acoustic matching layer 29 and greater than that of the second acoustic matching layer 32 and that exhibit piezoelectric properties are employed as the material of the acoustic wave receiving piezoelectric bodies 30. Fluorine series materials such as PVDF and P(VDF-TrFE) are preferred as the material of the acoustic wave receiving piezoelectric bodies 30. These materials have large receiving coefficients g, and have comparatively high reception sensitivity with respect to ultrasonic waves.

Various materials having an acoustic impedance less than that of the acoustic wave receiving piezoelectric bodies 30 and greater than that of the human body may be employed as the material of the second acoustic matching layer 32. Specific examples of such materials include epoxy series resins.

The acoustic lens 33 focuses ultrasonic waves output by the ultrasonic wave transmitting/receiving piezoelectric bodies onto observation target portions. The acoustic lens 33 is formed by silicone rubber, for example, and the thickness thereof is approximately 1 mm at most.

Various materials may be employed as the adhesive agent which is used when stacking each layer of the UT array 21. Epoxy series resins are preferable because they have superior acoustic transmissive properties and bonding strength, as well as being inexpensive, which is favorable from the viewpoint of cost.

Meanwhile, the pulse laser unit 70 is that which has a built in Q switch solid state laser. The pulse laser unit 070 is connected to the laser unit connecting section 72 of the portable ultrasonic wave observing device via a power cable 71. If a light output command is input to the operating section 14 of the portable ultrasonic wave observing device 10 when obtaining a photoacoustic image, the pulse laser unit 70 receives a predetermined trigger and outputs a pulsed laser beam. The pulsed laser beam propagates through bundled fibers 73 and is irradiated toward subjects from a light irradiating section 74 provided at the leading end of the ultrasound probe 11.

In the present embodiment, the light irradiating section 74 is constituted by the leading end portions of a plurality of optical fibers that constitute the bundled fibers 73. That is, the leading end portions of the optical fibers are provided at both sides of the UT array 21 (above and below the UT array in FIG. 1) and are configured to irradiate the pulsed laser beams output therefrom toward subjects as lines.

As illustrated in FIG. 3, the transmitting/receiving circuit 41 includes: a pulsar 42, a receiver 43; a first A/D converter 44; an image generating section 45; a Tx/Rx 46; a receiver 47; and a second A/D converter 48.

The pulsar 42 is connected to the lower electrode 27 via the Tx/Rx 46. The pulsar 42 outputs excitation pulses (pulsed voltages) to the lower electrode 27 that cause the ultrasonic wave transmitting/receiving piezoelectric bodies 28 to generate ultrasonic waves.

The receiver 43 is connected to the lower electrode 27 via the Tx/Rx 46. Received signals based on ultrasonic waves reflected by observation target portions are input to the receiver 43 from the ultrasonic wave transmitting/receiving piezoelectric bodies 28, and the received signals are amplified by the receiver 43.

The first A/D converter 44 administers A/D conversion on the received signals amplified by the receiver 43, to digitize the received signals. The received signals which are digitized by the first A/D converter 44 are input to the image generating section 45.

The pulsar 42 and the receiver 43 are connected to the Tx/Rx 46. The input and output of the pulsar 42 and the receiver 43 with respect to the Tx/Rx 46 are selectively switched.

The receiver 47 is connected to the upper electrode 31. The receiver 47 amplifies received signals from the acoustic wave receiving piezoelectric bodies 30 when obtaining photoacoustic images. That is, when obtaining a photoacoustic image, the pulsed laser beam is irradiated toward a subject by the pulse laser unit 70 in the manner described above. The portion of the subject which is irradiated by the pulsed laser beam generates acoustic waves, and the acoustic waves are detected by the acoustic wave receiving piezoelectric bodies 30. The second A/D converter 48 administers A/D conversion on received signals output by the receiver 47, to digitize the received signals. The received signals which are digitized by the second A/D converter 48 are input to the image generating section 45.

The image generating section generates ultrasound images based on received signals input from the first A/D converter 44 when obtaining ultrasound images, then outputs the generated ultrasound images to the monitor 15. In addition, the image generating section generates photoacoustic images based on received signals input from the second A/D converter 48 when obtaining photoacoustic images, then outputs the generated photoacoustic images to the monitor 15. Note that the components that constitute the transmitting/receiving circuit 41 other than the image generating section 45 are provided for each combination of ultrasonic wave transmitting/receiving piezoelectric bodies 28 and acoustic wave receiving piezoelectric bodies 30.

As described above, the ultrasonic wave transmitting/receiving piezoelectric bodies 28 formed by an inorganic material has extremely high sensitivity within a comparatively narrow bandwidth. In contrast, the acoustic wave receiving piezoelectric bodies 30 formed by the organic material has comparatively high detection sensitivity across an extremely wide frequency bandwidth. Thereby, the ultrasonic wave transmitting/receiving piezoelectric bodies 28 can detect reflected ultrasonic waves, which are limited to a comparatively low frequency range, at extremely high sensitivity, while the acoustic wave receiving piezoelectric bodies 30 can detect acoustic waves, the frequencies of which range over an extremely wide frequency bandwidth from low frequency to high frequency. Therefore, the ultrasonic wave diagnosis apparatus 2 of the present embodiment is capable of generating high ultrasound images and photoacoustic images having high image quality.

In addition, the first acoustic matching layer 29 is employed as an electrode common to the ultrasonic wave transmitting/receiving piezoelectric bodies 28 and the acoustic wave receiving piezoelectric bodies 30. Thereby, a UT array having a simple structure can be produced at low production cost compared to a case in which separate electrodes are employed. In addition, a metal nanoparticle containing resin is employed as the material of the first acoustic matching layer 29. Therefore, the first acoustic matching layer 29 exhibits high conductivity, and functions sufficiently as a common electrode.

Further, the resin which is employed as the material of the first acoustic matching layer 29 is a thermocuring resin that functions as an adhesive agent that adhesively attaches the acoustic wave receiving piezoelectric bodies 30 to the UT array 21. Therefore, the number of production steps can be decreased compared to a case in which an adhesive agent is coated onto a first acoustic matching layer after the first acoustic matching layer is formed, and then stacking the acoustic wave receiving piezoelectric bodies 30 thereon. Thereby, the UT array can be produced in a simple manner. In addition, an increase in the number of thin film electrodes can be suppressed, which prevents deterioration in yield.

Note that an example was described in which the ultrasonic wave transmitting/receiving piezoelectric bodies 28 that also receive ultrasonic waves are provided as the ultrasonic transducers that transmit ultrasonic waves. Alternatively, dedicated transmitting ultrasonic transducers that only transmit ultrasonic waves may be provided instead of the ultrasonic wave transmitting/receiving piezoelectric bodies 28. In this case, piezoelectric bodies dedicated to receiving ultrasonic waves will also be provided. In the probe of the present invention, the dedicated receiving piezoelectric bodies are also formed by an inorganic material.

If the transmission path that connects the upper electrode 31 and the receiver (amplifier) 47 becomes long, voltage drops in received signals between the upper electrode 31 and the receiver become great due to capacity resistance of the transmission path. If the amount of voltage drops of received signals becomes great, the image quality of ultrasound images based on ultrasonic waves received by the acoustic wave receiving piezoelectric bodies 30 will deteriorate, and the advantageous effect obtained by employing the acoustic wave receiving piezoelectric bodies 30 having high receiving sensitivity will be significantly reduced.

For this reason, it is preferable for the transmission path that connects the upper electrode 31 and the receiver 47 to be as short as possible, and preferable for the upper electrode 31 and the receiver 47 to be place in close proximity to each other. Specifically, the receiver 47 may be built in to the scanning head 18 instead of being provided in the portable ultrasonic wave observing device 10 as in the present embodiment.

Example 1

Next, Example 1, in which each layer of the UT array 21 is stacked, will be described. Chlorinated polyethylene rubber cut to a thickness of 1 cm was employed as the backing material 26. A FPC (Flexible Printed Circuit) was adhesively attached to the backing material 26 using a thermocuring epoxy resin.

C92H (by FUJI CERAMICS CORPORATION), which is a PZT series piezoelectric ceramic, was employed as the material of the ultrasonic wave transmitting/receiving piezoelectric bodies 28. Both surfaces of the ultrasonic wave transmitting/receiving piezoelectric bodies 28 were ground such that the thickness thereof became 260 µm. A metal film was formed on one surface of the ultrasonic wave transmitting/receiving piezoelectric bodies, by successively sputtering Ti, Pt, and Au thereon. The side of the ultrasonic wave transmitting/receiving piezoelectric bodies 28 having the metal film thereon was adhesively attached to the FPC on the backing material 26. A resin that contains silver nanoparticles was employed as the adhesive agent, which was thermocured. The acoustic impedance of the ultrasonic wave transmitting/receiving piezoelectric bodies 28 was approximately 31 Mrayl. Note that the FPC adhesively attached onto the backing layer 26 and the Ti, Pt, and Au metal film formed on the ultrasonic wave transmitting/receiving piezoelectric bodies 28 constitute the lower electrode 27.

A resin that contains silver nanoparticles (by Sumitomo Electric Industries, Ltd.) was coated on the ultrasonic wave transmitting/receiving piezoelectric bodies 28 at a thickness of $\lambda/4$ ($\lambda$ is the wavelength of ultrasonic waves) as the first acoustic matching layer 29. After coating, the first acoustic matching layer 29 was cured by being heated in an atmosphere at approximately 180° C. for one hour. After heating, the acoustic impedance of the first acoustic matching layer 29 was approximately 12 Mrayl.

PVDF, which has an acoustic impedance of 4.5 Mrayl, was employed as the material of the acoustic wave receiving piezoelectric bodies 30. The acoustic wave receiving piezoelectric bodies 30 were molded to a thickness of $\lambda/4$, and a solid electrode (metal film) was formed on one surface thereof. The surfaces of the acoustic wave receiving piezoelectric bodies 30 opposite the solid electrode were adhesively attached to the first acoustic matching layer 29. A resin that contains silver nanoparticles was employed as the adhesive agent. Note that the solid electrode formed on the acoustic wave receiving piezoelectric bodies 30 constitutes the upper electrode 31.

Then, an epoxy series resin having an acoustic impedance of 2 Mrayl was ground such that the thickness thereof became $\lambda/4$, then adhesively attached onto the upper electrode 31 as the second acoustic matching layer 32, using a thermocuring epoxy series adhesive agent. Similarly, the acoustic lens 33 was adhesively attached onto the second acoustic matching layer 32.

Note that in the following examples, structures which are the same as those of Example 1 will be omitted, and only structures which are different will be described.

Example 2

PMN-PT (a Pb (Mg, Nb) $O_3$—$PbTiO_3$ series material by JFE MINERAL Co., Ltd.), which is a relaxer series piezoelectric single crystal, was employed as the material of the ultrasonic wave transmitting/receiving piezoelectric bodies 28. Both surfaces of the ultrasonic wave transmitting/receiving piezoelectric bodies 28 were ground such that the thickness thereof became 240 µm. The acoustic impedance of the ultrasonic wave transmitting/receiving piezoelectric bodies 28 was approximately 22 Mrayl.

The first acoustic matching layer 29 was stacked in the same manner as in Example 1, and then cured by heating within an atmosphere at 160° C. for one hour. After heating, the acoustic impedance of the first acoustic matching layer 29 was approximately 11 Mrayl.

Comparative Example 1

Metal films were formed on both surfaces of the ultrasonic wave transmitting/receiving piezoelectric bodies 28 by successively sputtering Ti, Pt, and Au thereon. The ultrasonic wave transmitting/receiving piezoelectric bodies 28 having the metal films formed on both surfaces thereof were adhesively attached to the FPC on the backing material 26. A resin that contains silver nanoparticles was employed as the adhesive agent, and thermocuring was performed within an atmosphere at 100° C. for one hour. The acoustic impedance of the ultrasonic wave transmitting/receiving piezoelectric bodies 28 was approximately 31 Mrayl.

The first acoustic matching layer 29 was not provided in Comparative Example 1, and the metal films formed on the upper surfaces of the ultrasonic wave transmitting/receiving piezoelectric bodies 28 were employed as the upper electrode. In addition, the acoustic wave receiving piezoelectric bodies 30 were also not provided. Instead, an epoxy series resin having zirconia particles dispersed therein was ground to a thickness of $\lambda/4$, then stacked on the ultrasonic wave transmitting/receiving piezoelectric bodies 28 as an acoustic matching layer. A thermocuring epoxy series adhesive agent was employed as the adhesive agent, which was cured by heating.

Further, an epoxy series resin having an acoustic impedance of 3 Mrayl was ground such that the thickness thereof became $\lambda/4$, and was adhesively attached to the $\lambda/4$ thick layer of the epoxy series resin having zirconia particles dispersed therein using a thermocuring epoxy series adhesive agent as the second acoustic matching layer 32.

TABLE 1

|  | Transmitting/Receiving Piezoelectric Bodies | | First Acoustic Matching Layer | | Receiving Piezoelectric Bodies | | Second Acoustic Matching Layer | |
| --- | --- | --- | --- | --- | --- | --- | --- | --- |
|  | Material | Impedance (Mrayl) | Material | Impedance (Mrayl) | Material | Impedance (Mrayl) | Material | Impedance (Mrayl) |
| Example 1 | PZT series piezoelectric ceramic | 31 | Silver nanoparticle containing resin | 12 | PVDF | 4.5 | Epoxy series resin | 2 |
| Example 2 | Relaxer series piezoelectric single crystal | 22 | Silver nanoparticle containing resin | 11 | PVDF | 4.5 | Epoxy series resin | 2 |

TABLE 1-continued

| | Transmitting/Receiving Piezoelectric Bodies | | First Acoustic Matching Layer | | Receiving Piezoelectric Bodies | | Second Acoustic Matching Layer | |
|---|---|---|---|---|---|---|---|---|
| | Material | Impedance (Mrayl) | Material | Impedance (Mrayl) | Material | Impedance (Mrayl) | Material | Impedance (Mrayl) |
| Comparative Example 1 | PZT series piezoelectric ceramic | 31 | n/a | n/a | Zirconia particle dispersed epoxy series resin | 8 | Epoxy series resin | 3 |

Table 1 above summarizes the relationships among the materials and acoustic impedances (Mrayl) of each layer of the Examples and Comparative Example 1. Only Example 2 employs the relaxer series piezoelectric single crystal having an acoustic impedance of 22 Mrayl as the material of the ultrasonic wave transmitting/receiving piezoelectric bodies 28, while the other examples employs the PCT series piezoelectric ceramic having an acoustic impedance of 31 Mrayl as the material of the ultrasonic wave transmitting/receiving piezoelectric bodies 28.

In Examples 1 and 2, the material of the first acoustic matching layer 29 is the resin containing silver nanoparticles. The acoustic impedance of the first acoustic matching layer 29 is 12 Mrayl in Example 1, and 11 Mrayl in Example 2. In contrast, Comparative Example 1 is not equipped with the first acoustic matching layer 29.

In Examples 1 and 2, the material of the acoustic wave receiving piezoelectric bodies 30 is PVDF having an acoustic impedance of 4.5 Mrayl. In contrast, Comparative Example 1 is equipped with the epoxy series resin with zirconia particles dispersed therein having an acoustic impedance of 8 Mrayl instead of the acoustic wave receiving piezoelectric bodies 30.

Epoxy series resin is employed as the material of the second acoustic matching layer 32 in all of the examples. The acoustic impedance of the second acoustic matching layer 32 is 3 Mrayl in Comparative Example 1, and 2 Mrayl in the other examples.

A test was conducted to investigate the receiving sensitivities of UT arrays 21 produced with Examples 1 and 2 as well as Comparative Example 1. The waveforms of ultrasonic waves become distorted as they propagate, and will include harmonic wave components, which are integer multiples of the frequencies of fundamental waves. Examples 1 and 2 received secondary harmonic waves (acoustic waves having a frequency twice the frequency of fundamental waves) in addition to the fundamental waves at high sensitivity.

In contrast, Comparative Example 1 was capable of receiving fundamental waves in the case that the transmission frequency was a predetermined frequency or greater, but was not capable of receiving secondary harmonic waves. Note that it was possible to receive secondary harmonic waves by decreasing the transmission frequency. However, the transmission frequency in such cases was insufficient to perform ultrasound imaging.

The above embodiment was described as a convex electronic scanning external ultrasound probe. The present invention may alternatively be applied to an ultrasound probe of the radial electronic scanning type, or of a mechanical scanning type that rotate, swing, or slide a single UT. The present invention may also be applied to internal ultrasound probes which are inserted into the forceps channels of electronic endoscopes, and to ultrasound endoscopes in which ultrasound probes are integrated with electronic endoscopes.

In addition, the laser light source that constitutes the pulse laser unit is not limited to the solid state laser which was employed in the embodiment described above. Other laser light sources, such as an AlGaAs semiconductor laser having a maximum oscillating wavelength of 800 nm and an InGaAs semiconductor laser having a maximum oscillating wavelength of 900 nm may alternatively be employed. Further, a combination of a light amplifying laser light source that employs a semiconductor laser as a seed light source and an optical wavelength converting element may also be employed as the laser light source. More specifically, a combination of a semiconductor laser that outputs a laser beam having a wavelength of approximately 1560 nm, a fiber amplifier constituted by a polarization preserving Er (erbium) doped optical fiber, and a SHG (second harmonic generating) element that converts the amplified laser beam to a second harmonic wave of approximately 780 nm may be employed as the laser light source.

What is claimed is:

1. A probe for a photoacoustic imaging apparatus, comprising:
    a light irradiating section that outputs light to be irradiated onto a subject such that photoacoustic waves are generated;
    an acoustic wave generating section that generates and outputs acoustic waves to be irradiated onto the subject:
    first piezoelectric bodies that detect the acoustic waves which are reflected by the subject; and
    second piezoelectric bodies that detect photoacoustic waves generated within the subject due to irradiation of the light;
    piezoelectric bodies made from an inorganic material being employed as the first piezoelectric bodies; and
    piezoelectric bodies made from an organic material being employed as the second piezoelectric bodies.

2. A probe for a photoacoustic imaging apparatus as defined in claim 1, further comprising:
    an acoustic matching layer that also functions as an electrode common to the first and second piezoelectric bodies, formed between the first and second piezoelectric bodies.

3. A probe for a photoacoustic imaging apparatus as defined in claim 2, wherein:
    the acoustic impedance of the acoustic matching layer is lower than the acoustic impedance of the first piezoelectric bodies and higher than the acoustic impedance of the second piezoelectric bodies.

4. A probe for a photoacoustic imaging apparatus as defined in claim 1, wherein:
    the second piezoelectric bodies are provided more toward the subject than the first piezoelectric bodies.

5. A probe for a photoacoustic imaging apparatus as defined in claim 2, wherein:
the acoustic matching layer contains metal.

6. A probe for a photoacoustic imaging apparatus as defined in claim 5, wherein:
the metal includes silver.

7. A probe for a photoacoustic imaging apparatus as defined in claim 5, wherein:
the acoustic matching layer is a composite of an organic material and a metal.

8. A probe for a photoacoustic imaging apparatus as defined in claim 7, wherein:
the organic material of the acoustic matching layer has adhesive properties.

9. A probe for a photoacoustic imaging apparatus as defined in claim 5, wherein:
the metal is metal nanoparticles.

10. A probe for a photoacoustic imaging apparatus as defined in claim 2, wherein:
the acoustic matching layer is one of a material having relatively low conductive properties or a material having no conductive properties, the surface of the material being covered with a material having conductive properties.

11. A probe for a photoacoustic imaging apparatus as defined in claim 1, wherein:
the first piezoelectric bodies are formed as long strips in a first direction.

12. A probe for a photoacoustic imaging apparatus as defined in claim 11, wherein:
a plurality of the first piezoelectric bodies are arranged in a direction perpendicular to the first direction.

13. A probe for a photoacoustic imaging apparatus as defined in claim 1, wherein:
the thickness of the first piezoelectric bodies is within a range from 0.1 mm to 0.5 mm.

14. A probe for a photoacoustic imaging apparatus as defined in claim 1, wherein:
the second piezoelectric bodies are formed as long strips in a first direction.

15. A probe for a photoacoustic imaging apparatus as defined in claim 14, wherein:
a plurality of the second piezoelectric bodies are arranged in a direction perpendicular to the first direction.

16. A probe for a photoacoustic imaging apparatus as defined in claim 1, wherein:
the second piezoelectric bodies are electrically divided by a plurality of electrodes, which are patterned into long strips in a first direction, into a plurality of piezoelectric bodies which are arranged in a direction perpendicular to the first direction.

17. A probe for a photoacoustic imaging apparatus as defined in claim 1, wherein:
the thickness of the second piezoelectric bodies is within a range from 0.05 mm to 0.3 mm.

18. A probe for a photoacoustic imaging apparatus as defined in claim 1, further comprising:
an acoustic lens that focuses acoustic waves onto an observation target portion, provided more toward the subject than the first piezoelectric bodies.

19. A photoacoustic imaging apparatus equipped with a probe for a photoacoustic imaging apparatus as defined in claim 1.

20. A photoacoustic imaging method that employs a probe for a photoacoustic imaging apparatus as defined in claim 1, that obtains acoustic images based on signals output by the first piezoelectric bodies, and obtains photoacoustic images based on signals output by the second piezoelectric bodies.

* * * * *